United States Patent
Buder et al.

(10) Patent No.: US 9,474,868 B2
(45) Date of Patent: Oct. 25, 2016

(54) SINGLE-USE SYRINGE ASSEMBLY

(75) Inventors: Christopher Buder, Sharon, MA (US); Kurt E. Green, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 1634 days.

(21) Appl. No.: 12/408,998

(22) Filed: Mar. 23, 2009

(65) Prior Publication Data

US 2009/0247949 A1    Oct. 1, 2009

Related U.S. Application Data

(60) Provisional application No. 61/040,984, filed on Mar. 31, 2008.

(51) Int. Cl.
  *A61M 5/50*    (2006.01)
  *A61M 5/315*   (2006.01)
  *A61M 5/32*    (2006.01)

(52) U.S. Cl.
  CPC .......... *A61M 5/508* (2013.01); *A61M 5/5086* (2013.01); *A61M 2005/323* (2013.01); *A61M 2205/273* (2013.01); *A61M 2205/276* (2013.01)

(58) Field of Classification Search
  CPC .... A61M 5/50; A61M 5/508; A61M 5/5066; A61M 5/321; A61M 5/5086; A61M 5/322; A61M 2205/27; A61M 2205/273; A61M 2205/276; A61M 5/31591; A61M 5/3148; A61M 5/31511; A61M 5/5013; A61M 2005/3106
  USPC ................................................. 604/110, 111
  See application file for complete search history.

(56) References Cited

U.S. PATENT DOCUMENTS 4,233,975 A * 11/1980 Yerman ................. A61M 5/286
                                                       604/110
4,775,364 A    10/1988 Alles
              (Continued)

FOREIGN PATENT DOCUMENTS

EP    0 325 049      7/1989
EP    0925083        3/2009
              (Continued)

OTHER PUBLICATIONS

European Patent Search Report dated Oct. 18, 2011 for European Patent Appln. No. EP 11 00 7214.

*Primary Examiner* — Bhisma Mehta
*Assistant Examiner* — Jenna Zhang

(57) ABSTRACT

A single-use syringe assembly is disclosed which includes a syringe body defining a fluid reservoir and including an engagement surface, a plunger assembly including a plunger rod and a sealing member supported on a distal end of the plunger rod, and a releasable member having a proximal end releasably positioned within a sealing member throughbore and a distal end configured to engage the engagement surface of the syringe body when the sealing member is moved to the advanced position. The proximal end of the releasable member being configured to seal the sealing member throughbore. The releasable member is configured such that a force required to remove the distal end of the releasable member from engagement with the engagement surface of the syringe body is greater than the force required to disengage the proximal end of the releasable member from the sealing member throughbore. As such, upon movement of the sealing member from the advanced position to the retracted position, the proximal end of the releasable member is disengaged from the sealing member throughbore to unseal the throughbore.

13 Claims, 4 Drawing Sheets

(56) References Cited

U.S. PATENT DOCUMENTS

| | | | |
|---|---|---|---|
| 4,919,652 A | 4/1990 | Alter et al. | |
| 4,950,240 A | 8/1990 | Greenwood et al. | |
| 5,000,735 A * | 3/1991 | Whelan | A61M 5/50 604/110 |
| 5,004,460 A | 4/1991 | Gimeno | |
| 5,045,063 A * | 9/1991 | Spielberg | A61M 5/5013 604/110 |
| 5,047,017 A | 9/1991 | Koska | |
| 5,135,512 A | 8/1992 | Mazurik et al. | |
| 5,201,709 A * | 4/1993 | Capra | A61M 5/5066 604/110 |
| 5,205,824 A | 4/1993 | Mazur | |
| 5,242,400 A | 9/1993 | Blake, III et al. | |
| 5,259,840 A | 11/1993 | Boris | |
| 5,304,138 A | 4/1994 | Mercado | |
| 5,308,331 A | 5/1994 | Avila et al. | |
| 5,318,537 A | 6/1994 | Van Der Merwe | |
| 5,344,403 A | 9/1994 | Lee | |
| 5,346,474 A | 9/1994 | King | |
| 5,380,285 A | 1/1995 | Jenson | |
| 5,401,249 A | 3/1995 | Shields | |
| 5,423,756 A | 6/1995 | van der Merwe | |
| 5,478,314 A * | 12/1995 | Malenchek | A61M 5/5066 604/110 |
| 5,531,691 A | 7/1996 | Shonfeld et al. | |
| 5,709,659 A | 1/1998 | Bennwik et al. | |
| 5,814,017 A * | 9/1998 | Kashmer | A61M 5/5013 604/110 |
| 5,833,660 A * | 11/1998 | Nathan | A61M 5/5013 604/110 |
| 6,267,749 B1 | 7/2001 | Miklos et al. | |
| 6,599,269 B1 * | 7/2003 | Lewandowski | A61M 5/5013 604/110 |
| 6,790,197 B2 | 9/2004 | Kosinski et al. | |
| 6,846,301 B2 * | 1/2005 | Smith | A61M 5/3234 604/110 |
| 6,872,191 B2 * | 3/2005 | Lo | A61M 5/5013 604/110 |
| 7,320,680 B2 * | 1/2008 | Shue | A61M 5/5066 604/110 |
| 2005/0240149 A1 * | 10/2005 | Lu | A61M 5/5013 604/110 |
| 2005/0261627 A1 * | 11/2005 | Shue | A61M 5/5066 604/110 |
| 2005/0277880 A1 * | 12/2005 | Shue | A61M 5/31531 604/110 |
| 2006/0064060 A1 * | 3/2006 | Lin | A61M 5/5013 604/110 |

FOREIGN PATENT DOCUMENTS

| | | |
|---|---|---|
| WO | WO 03/051434 | 6/2003 |
| WO | WO 2006/136769 | 12/2006 |

* cited by examiner

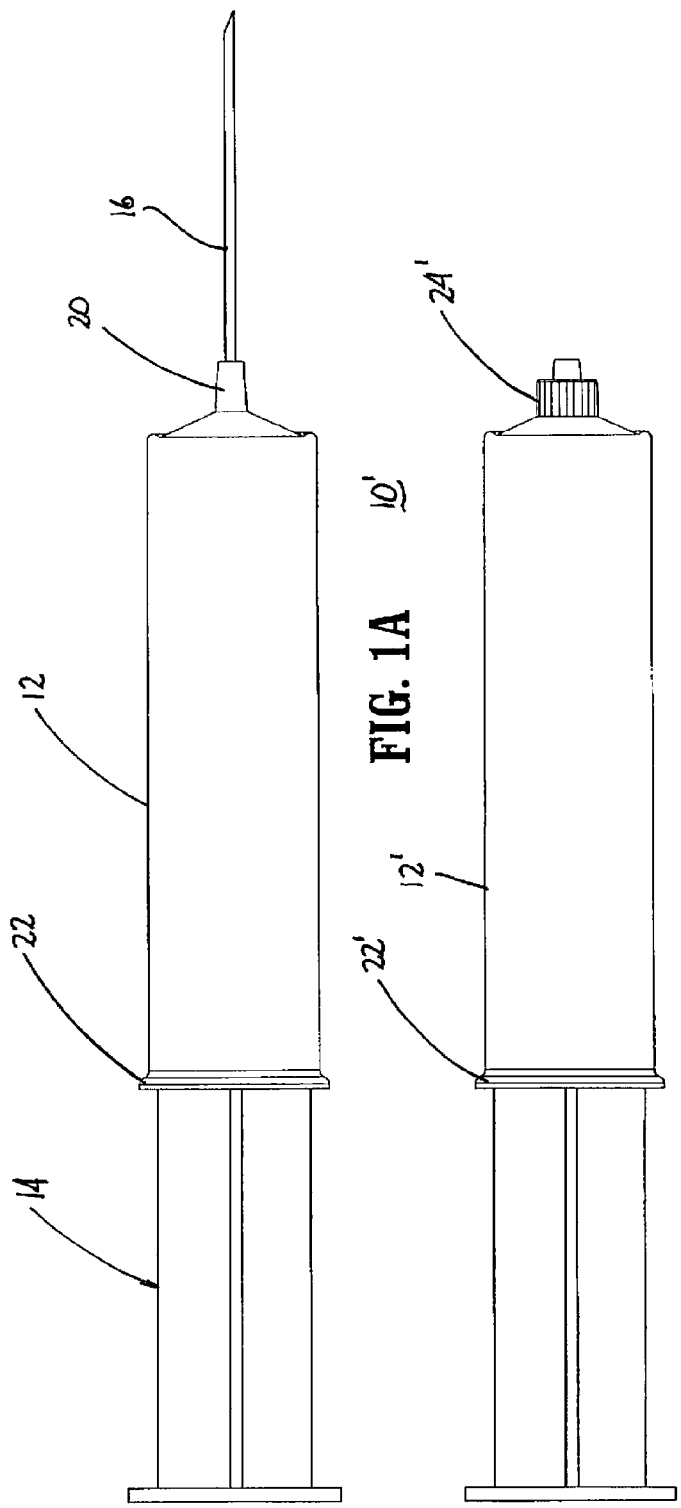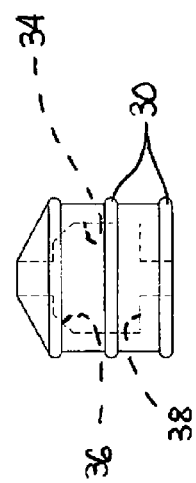
FIG. 1A
FIG. 1B
FIG. 2A

SINGLE-USE SYRINGE ASSEMBLY

CROSS REFERENCE TO RELATED APPLICATION

This patent application claims priority to U.S. Provisional Application Ser. No. 61/040,984, filed Mar. 31, 2008, which is incorporated herein in its entirety by reference.

TECHNICAL FIELD

The present disclosure relates to single-use medical syringes and, more particularly, to single-use syringes which include a mechanism for disabling a plunger assembly of the syringe after an injection stroke of the plunger has been completed.

DESCRIPTION OF RELATED ART

Single-use syringes are well known in the medical arts. A single-use syringe prevents reuse of the syringe to minimize exposure of patients to HIV, hepatitis and other blood-borne pathogens. A variety of different types of single-use syringes are known. These include syringes having frangible plunger disabling mechanisms and those having complex locking elements, e.g., precision metal stampings. Those with complex locking mechanisms are expensive and require complicated manufacturing procedures. With regard to those syringes which include frangible plunger disabling mechanisms, it has been difficult to engineer, design and manufacture a frangible plunger assembly which can operate to eject fluid from a syringe and has a break force which assures disablement of the plunger assembly.

Accordingly, a continuing need exists in the medical arts for a simple, reliable, robust single-use syringe.

BRIEF DESCRIPTION OF THE DRAWINGS

Various embodiments of the presently disclosed single-use syringe assembly are disclosed herein with reference to the drawings, wherein:

FIG. 1A is a side perspective view of one embodiment of the presently disclosed single-use syringe assembly having a staked needle;

FIG. 1B is a side perspective view of another embodiment of the presently disclosed single-use syringe assembly having a luer-type connector;

FIG. 2A is a side view of the sealing member of the single-use syringe assembly shown in FIG. 2;

SUMMARY

Figure 2:
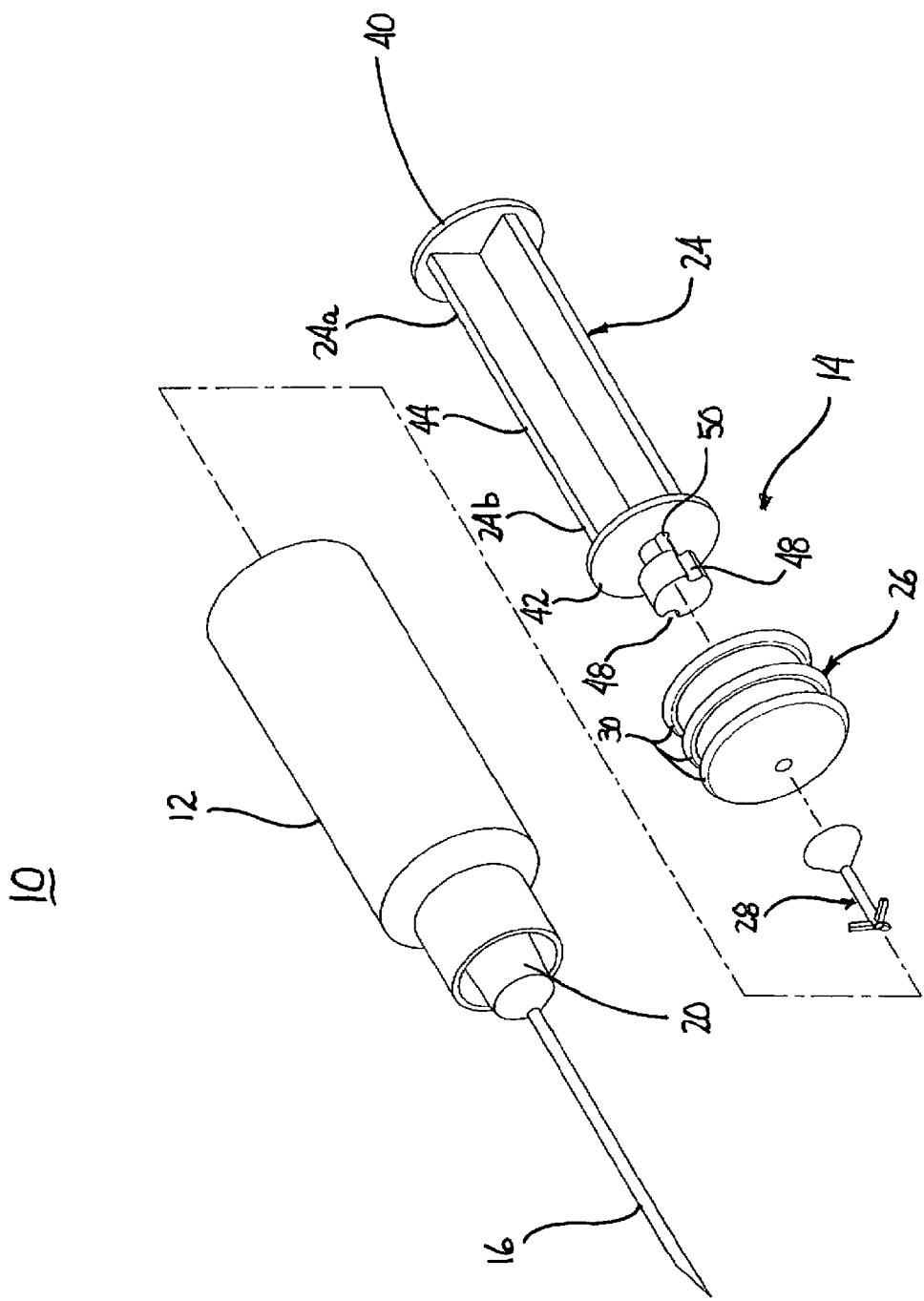
FIG. 2 is an exploded side perspective view of the single-use syringe assembly shown in FIG. 1A.

A single-use syringe assembly is disclosed which includes a syringe body which defines a fluid reservoir. The reservoir may be filled with a fluid during construction and/or assembly of the syringe assembly. A distal end of the reservoir defines an engagement surface. A plunger assembly includes a plunger rod and a sealing member supported on a distal end of the plunger rod. The sealing member defines a throughbore and is movably positioned within the fluid reservoir from a retracted position to an advanced position. A releasable member has a proximal end releasably positioned within the sealing member throughbore and a distal end configured to engage the engagement surface of the syringe body when the sealing member is moved to the advanced position. The proximal end of the releasable member is configured to seal the sealing member throughbore. The releasable member is configured such that a force required to remove the distal end of the releasable member from engagement with the engagement surface of the syringe body is greater than the force required to disengage the proximal end of the releasable member from the sealing member throughbore. As such, upon movement of the sealing member from the advanced position to the retracted position, the proximal end of the releasable member is disengaged from the sealing member throughbore to unseal the throughbore.

In one embodiment, the engagement surface of the syringe body defines a substantially annular channel. The distal end of the releasable member may include one or more deformable fingers which are dimensioned to be retained within the annular channel. In one embodiment, the one or more deformable fingers includes three deformable fingers.

The syringe body can include a needle support which defines a tapered throughbore. In one embodiment, the annular channel is positioned within the tapered throughbore. A needle cannula can be supported on the needle support. Alternatively, a luer connector can be formed on the distal end of the syringe body.

In one embodiment, the proximal end of the releasable member defines a frustoconically shaped member which is dimensioned to be releasably received within the sealing member throughbore, and the sealing member throughbore is defined by tapered distal walls such that the frustoconically shaped member engages the tapered distal walls to seal the throughbore.

In one embodiment, the distal end of the plunger rod has a stepped extension member which is dimensioned to be received in the sealing member throughbore to abut with the proximal end of the frustoconically shaped member. Engagement between the stepped extension member and the frustoconically shaped member maintains the frustoconically shaped member in sealing engagement with the tapered distal walls defining the sealing member throughbore. The stepped extension member can include one or more external grooves which are positioned in communication with the sealing member throughbore to define a fluid flowpath from a distal side of the sealing member to a proximal side of the sealing member.

In one embodiment, the plunger rod includes a disc positioned proximally of the stepped extension member and configured to engage a proximal surface of the sealing member. The disc can define holes which communicate with the one or more external grooves in the stepped extension member.

DETAILED DESCRIPTION OF EMBODIMENTS

Embodiments of the presently disclosed single-use plunger and syringe assembly will now be described in detail with reference to the drawings wherein like reference numerals designate identical or corresponding elements in each of the several views. In this description, the term proximal is generally used to indicate the relative nearness of a referenced item to a clinician using the assembly and the term distal is used to indicate the remoteness of a referenced item to a clinician using the device.

FIG. 1A illustrates one embodiment of the presently disclosed single-use syringe assembly shown generally as 10. Briefly, single-use syringe assembly 10 includes a syringe body 12, a plunger assembly 14, and a needle cannula 16. Syringe body 12 defines a fluid reservoir 18 (FIG. 3) and includes a distally positioned needle support 20 and a proximally positioned flange 22. Needle 16 is secured within needle support 20 in a known manner at a distal end of body 12. In an alternative embodiment of the presently disclosed single-use syringe assembly shown generally as 10' in FIG. 1B, a distal end of syringe body 12' includes a luer-type connector 24' which is configured to engage a luer-connector (not shown) of a needle hub assembly (not shown) or an indwelling catheter (not shown). A proximal end of syringe body 12' includes a flange 22'. Syringe assembly 10' also includes a plunger assembly 14' which is substantially identical to plunger assembly 14.

Referring also to FIG. 2, plunger assembly 14 includes a plunger rod 24, a sealing member 26 and a releasable member 28. Sealing member 26 is configured to be slidably received within fluid reservoir 18 (FIG. 3) of syringe body 12 and includes one or more annular ribs 30 which sealingly engage an inner wall 32 (FIG. 3) of syringe body 12 defining reservoir 18. In one embodiment, sealing member 26 is formed from an elastomeric material although other suitable materials of construction are envisioned. Sealing member 26 defines a stepped throughbore 34 (FIG. 2A) having tapered distal walls 36 and proximal walls 38 which are substantially orthogonal to a longitudinal axis of syringe body 12.

Figure 2D:
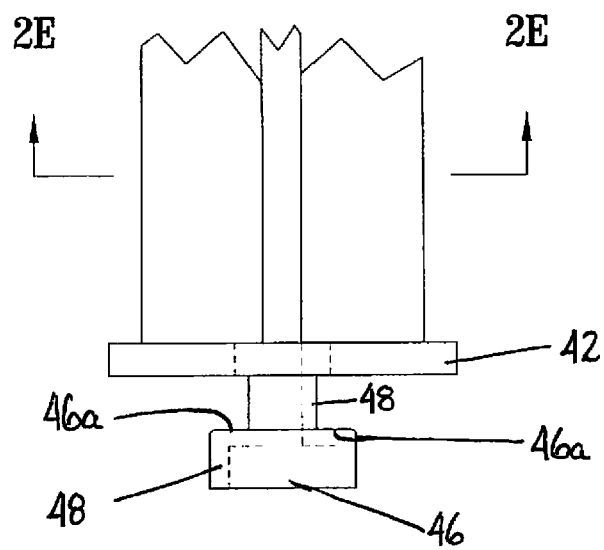
FIG. 2D is an enlarged, cutaway view of the distal end of the plunger rod of the single-use syringe assembly shown in FIG. 2.
Figure 2E:
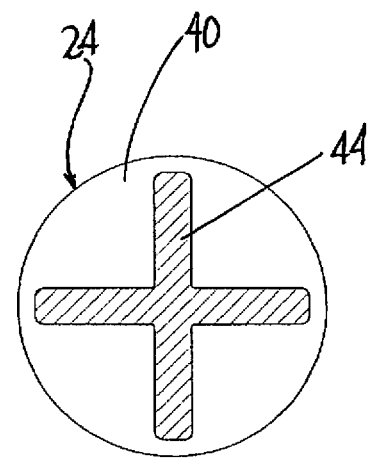
FIG. 2E is a cross-sectional view taken along section lines 2E-2E of FIG. 2D.

Plunger rod 24 has a proximal end 24a having a finger engagement member 40 and a distal end 24b defining a disc 42. A body portion 44 connects engagement member 40 with disc 42. In one embodiment, body portion 44 is t-shaped (FIG. 2E). Alternatively, other body portion configurations are envisioned. A stepped extension member 46 (FIG. 2D) extends distally from disc 42 and is configured to be received within a proximal portion of stepped throughbore 34 of sealing member 26. Extension member 46 defines a shoulder or step 46a which abuts proximal walls 38 (FIG. 2A) of sealing member 26 to resist separation of plunger rod 24 from sealing member 26. As illustrated in FIG. 2, grooves 48 are formed along an outer surface of extension member 46. Grooves 48 communicate with openings 50 formed in disc 42. The purpose of grooves 48 and openings 50 will be discussed in further detail below.

Figure 2B:
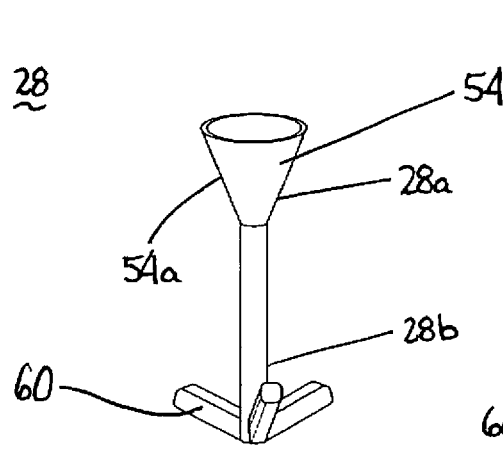
FIG. 2B is a side perspective view of the releasable member of the single-use syringe assembly shown in FIG. 2.
Figure 2C:
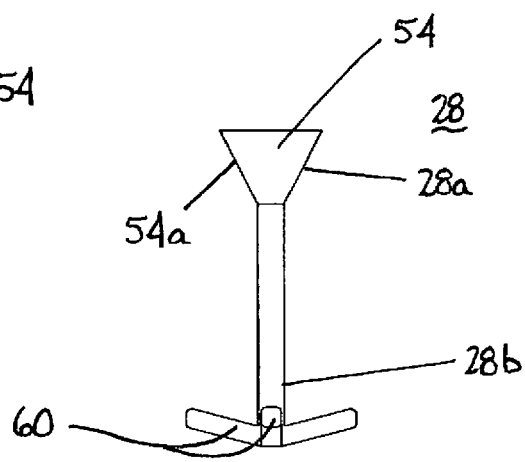
FIG. 2C is a side view of the releasable member of the single-use syringe assembly shown in FIG. 2B.

Referring to FIGS. 2, 2B and 2C, releasable member 28 includes a proximal end 28a configured to be releasably received within distal portion of stepped throughbore 34 and a distal end 28b configured to engage an engagement surface 52 (FIG. 3) defined on an internal surface of syringe body 12. In one embodiment, engagement surface 52 includes an annular channel. In one embodiment, proximal end 28a of releasable member 28 includes a frustoconically-shaped member 54 which has a distally tapered surface 54a. Frustoconical member 54 of releasable member 28 is dimensioned to be received within the distal portion of stepped throughbore 34 such that tapered surface 54a is maintained in sealing engagement with tapered distal walls 36 of stepped throughbore 34 by a distal face of extension member 46.

Figure 3:
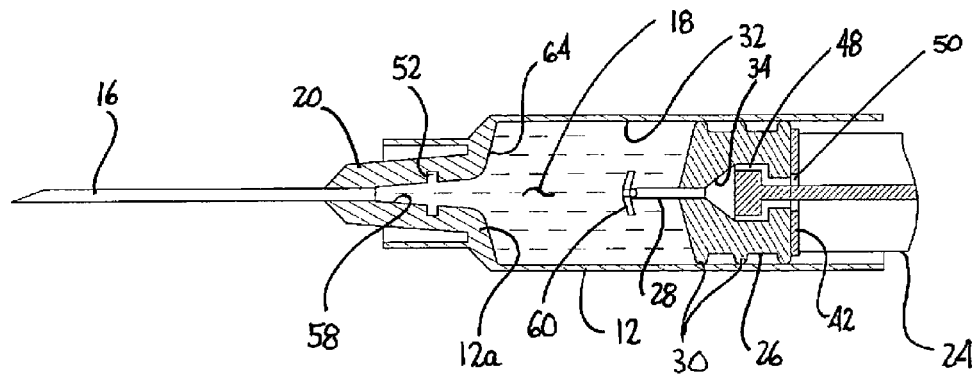
FIG. 3 is a cross-sectional view of the single-use syringe assembly shown in FIG. 1A with the plunger assembly in a retracted position prior to actuation of the syringe assembly.

Referring also to FIG. 3, needle support 20 defines a tapered throughbore 58 in a distal end of fluid reservoir 18 which fluidly communicates reservoir 18 with needle or cannula 16. In one embodiment, annular channel 52 is positioned within throughbore 58 of needle support 20 and distal end 28b of releasable member 28 includes one or more flexible or deformable fingers 60. Although three fingers are illustrated in FIG. 2, one or more fingers may be provided. Deformable fingers 60 are dimensioned such that fingers 60 are deformed rearwardly and inwardly as distal end 28b of releasable member 28 is moved through throughbore 58. When fingers 60 are advanced to a position aligned with annular channel 52 defined within support 20, fingers 60 flex or move outwardly into annular channel 52. Fingers 60 are configured to provide resistance to proximal movement of releasable member 28. This resistance to proximal movement effected by receipt of fingers 60 within annular channel 52 defined within support 20 is greater than the force required to pull proximal end 28a from stepped throughbore 34 of sealing member 26. Thus, when sealing member 26 is moved proximally by pulling plunger rod 24 proximally after fingers 60 have been received in annular channel 52, proximal end 28a of releasable member 28 is pulled from stepped throughbore 34 to disengage releasable member 28 from sealing member 26. It is also contemplated that distal end 28b of releasable member 28 may be formed in a manner that provides for an interference fit with tapered throughbore 58 and that the interference fit would provide sufficient resistance to proximal movement of releasable member 28, obviating the need for fingers 60 and/or annular channel 52.

When releasable member 28 is disengaged from sealing member 26, the distal opening of throughbore 34 is no longer sealed by proximal end 28a of releasable member 28. Thus, the portion of reservoir 18 defined between sealing member 26 and a distal end 12a of syringe body 12 fluidly communicates with grooves 48 in distal extension 46 and openings 50 in disc 42 of plunger rod 24. The significance of this will be described in further detail below.

It is noted that releasable member 28 is separated from sealing member 26 because the force required to disengage fingers 60 from annular channel 52 in a proximal direction is greater than the force required to separate proximal end 28a from stepped throughbore 34 of sealing member 26. As such, only a minimal force need be required to effect separation of releasable member 28 from sealing member 26, e.g., less than one pound. Furthermore, releasable member 28 need not be formed of a high strength, cost prohibitive material since the forces acting upon releasable member 28 are minimal. It is envisioned that releasable member 28 may assume a variety of configurations different from the configuration described herein.

Figure 4:
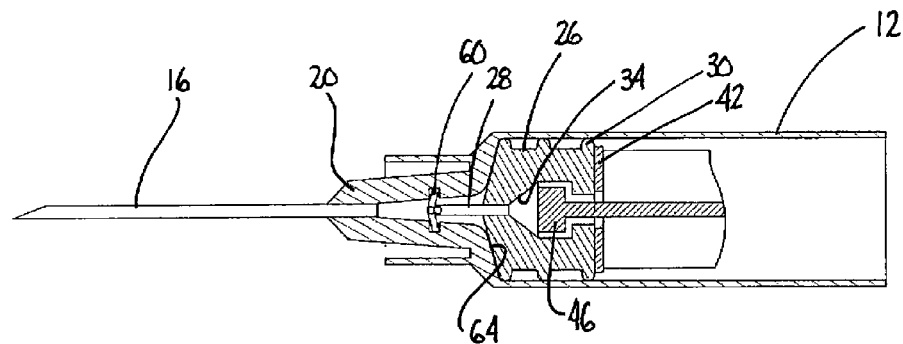
FIG. 4 is a cross-sectional view of the single-use syringe assembly shown in FIG. 1A with the plunger in the advanced position.
Figure 5:
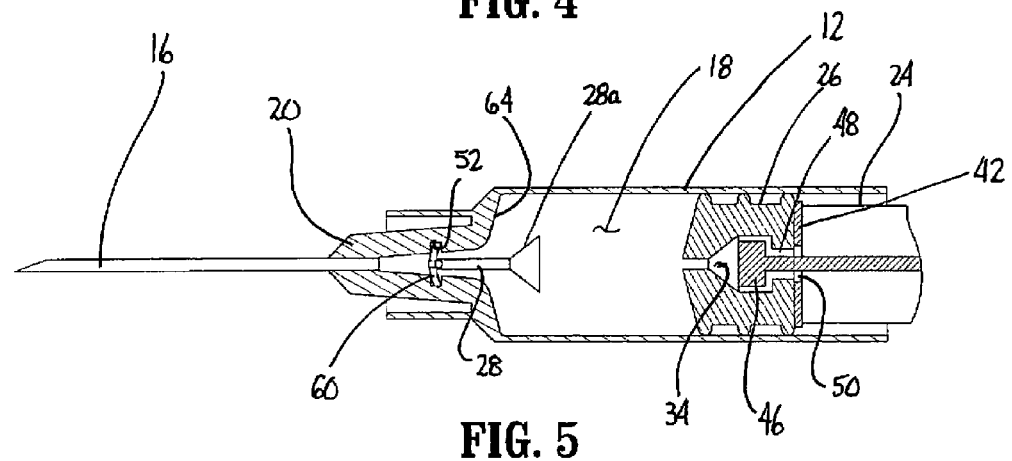
FIG. 5 is a cross-sectional view of the single-use syringe assembly shown in FIG. 1A with the plunger in the retracted position subsequent to actuation of the syringe assembly.

Referring to FIGS. 3 to 5, when plunger rod 24 is actuated to advance sealing member 26 from a retracted position (FIG. 3) to an advanced position (FIG. 4), releasable member 28 is advanced distally as fluid within reservoir 18 is forced from reservoir 18 though needle 16. When distal end 28b of releasable member 28 enters support throughbore 58 and is advanced to a position aligned with annular channel 52, fingers 60 move into annular channel 52 (FIG. 4).

In one embodiment, fingers 60 are positioned to move into annular channel 52 to prevent sealing member 26 from bottoming out on a distal inner face 64 of syringe body 12. If sealing member 26 is compressed against distal inner face 64 of syringe body 12 by pressing on plunger rod 24, sealing member 26 may deform into support throughbore 58. When plunger rod 24 is subsequently released, movement of sealing member 26 from support throughbore will pull a slight vacuum within support throughbore 58 causing fluid, e.g., blood, to reflux or flow into needle 16 or into medical apparatus to which syringe assembly 10' (FIG. 1B) is attached, e.g., an indwelling catheter. For reasons known in the medical arts, this may cause clotting of the catheter and increase the risks of infection. Thus, by positioning fingers 60 to move into channel 52 prior to sealing member 26 engaging distal face 64 of syringe body 12, fluid reflux into needle 16 or an indwelling catheter can be minimized.

As discussed above, when plunger rod 24 is retracted to move sealing member 26 proximally within reservoir 18 of syringe body 12 (FIG. 5), proximal end 28a of releasable member 28 is pulled from stepped throughbore 34. This occurs because the releasable member 28 is configured such that the force required to disengage fingers 60 from annular channel 52 is greater than the force required to disengage proximal end 28a of releasable member 28 from stepped throughbore 34 of sealing member 26. As discussed above, each of these forces may be designed to be minimal, e.g., less than two pounds. When proximal end 28a of releasable member 28 is removed from stepped throughbore 34 of sealing member 26, a fluid flowpath is defined through sealing member 26 via throughbore 34, grooves 48 and openings 50. Thus, if an attempt was made to draw a fluid into reservoir 18 and reuse assembly 10 or 10', minimal or substantially no fluid would be drawn into reservoir 18 by sealing member 26 due to the flow of air through the flowpath created through the sealing member.

It will be understood that various modifications may be made to the embodiments disclosed herein. For example, it is envisioned that the releasable member may be configured to engage the distal end of the syringe body in a variety of different manners and/or at different locations. Thus, the configuration of releasable member and of the engagement surface of the syringe body may be changed in accordance with the disclosure herein. Therefore, the above description should not be construed as limiting, but merely as exemplifications of preferred embodiments. Those skilled in the art will envision other modifications within the scope and spirit of the claims appended hereto.

What is claimed is:

1. A single-use syringe assembly comprising:
a syringe body defining a fluid reservoir, a distal end of the reservoir defining an engagement surface;
a plunger assembly including a plunger rod and a sealing member supported on a distal end of the plunger rod, the sealing member defining a throughbore and being movably positioned within the fluid reservoir from a retracted position to an advanced position;
a releasable member having a proximal end releasably positioned within the sealing member throughbore and a distal end configured to engage the engagement surface of the syringe body when the sealing member is moved to the advanced position, the proximal end of the releasable member being configured to seal the sealing member throughbore;
wherein the releasable member is configured such that a force required to remove the distal end of the releasable member from engagement with the engagement surface of the syringe body is greater than the force required to disengage the proximal end of the releasable member from the sealing member throughbore, wherein upon movement of the sealing member from the advanced position to the retracted position, the proximal end of the releasable member is disengaged from the sealing member throughbore to unseal the sealing member throughbore and to allow fluid to flow through the entire sealing member throughbore.

2. The single-use syringe assembly according to claim 1, wherein the engagement surface of the syringe body defines a substantially annular channel.

3. The single-use syringe assembly according to claim 2, wherein the distal end of the releasable member includes one or more deformable fingers which are dimensioned to be retained within the annular channel.

4. The single-use syringe assembly according to claim 3, wherein the one or more deformable fingers includes three deformable fingers.

5. The single-use syringe assembly according to claim 2, wherein the syringe body includes a needle support which defines a tapered throughbore, the annular channel being positioned within the tapered throughbore.

6. The single-use syringe assembly according to claim 5, further including a needle cannula supported on the needle support.

7. The single-use syringe assembly according to claim 5, further including a luer connector formed on the distal end of the syringe body.

8. The single-use syringe assembly according to claim 1, wherein the proximal end of the releasable member defines a frustoconically shaped member which is dimensioned to be releasably received within the sealing member throughbore.

9. The single-use syringe assembly according to claim 8, wherein the sealing member throughbore is defined by tapered distal walls, the frustoconically shaped member being configured to engage the tapered distal walls to seal the sealing member throughbore.

10. The single-use syringe assembly according to claim 9, wherein the distal end of the plunger rod has a stepped extension member which is dimensioned to be received in the sealing member throughbore to abut with the proximal end of the frustoconically shaped member, wherein engagement between the stepped extension member and the frustoconically shaped member maintains the frustoconically shaped member in sealing engagement with the tapered distal walls defining the sealing member throughbore.

11. The single-use syringe assembly according to claim 10, wherein the stepped extension member includes one or more external grooves, the sealing member throughbore and the one or more external grooves defining a fluid flowpath from a distal side of the sealing member to a proximal side of the sealing member.

12. The single-use syringe assembly according to claim 11, wherein the plunger rod includes a disc positioned proximally of the stepped extension member, the disc being configured to engage a proximal surface of the sealing member.

13. The single-use syringe assembly according to claim 12, wherein the disc defines holes which communicate with the one or more external grooves in the stepped extension member.

* * * * *